US009652586B2

(12) United States Patent
Li et al.

(10) Patent No.: US 9,652,586 B2

(45) Date of Patent: May 16, 2017

(54) METHOD AND SYSTEM FOR FASTER AND MORE SENSITIVE HOMOLOGY SEARCHING

(75) Inventors: Ming Li, Santa Barbara, CA (US); Bin Ma, Waterloo (CA); John Tromp, Waterloo (CA)

(73) Assignee: BIOINFORMATICS SOLUTIONS INC., Waterloo, Ontario (CA)

( * ) Notice: Subject to any disclaimer, the term of this patent is extended or adjusted under 35 U.S.C. 154(b) by 1274 days.

(21) Appl. No.: 11/561,327

(22) Filed: Nov. 17, 2006

(65) Prior Publication Data

US 2007/0088510 A1 Apr. 19, 2007

Related U.S. Application Data

(62) Division of application No. 10/236,339, filed on Sep. 6, 2002, now abandoned.

(60) Provisional application No. 60/338,480, filed on Dec. 3, 2001.

(30) Foreign Application Priority Data

Sep. 7, 2001 (CA) ..................................... 2357263

(51) Int. Cl.

| | |
|---|---|
| ***G06G 7/58*** | (2006.01) |
| ***G06F 19/22*** | (2011.01) |
| ***G06F 19/24*** | (2011.01) |
| *G01N 33/48* | (2006.01) |

(52) U.S. Cl.
CPC .............. *G06F 19/22* (2013.01); *G06F 19/24* (2013.01)

(58) Field of Classification Search
None
See application file for complete search history.

(56) References Cited

U.S. PATENT DOCUMENTS

2002/0164588 A1 11/2002 Eisenberg et al. ................ 435/6

OTHER PUBLICATIONS

Kent et al. "Conservation, Regulation, Synteny, and Introns in a Large-scale C. briggsae—C. elegans Genomic Aignment", Genome Research (2000) vol. 10, pp. 1115-1125.*

Preparata, F., and Upfal, E. Sequencing-by-hybridization at the information-theory bound: an optimal algorithm. In Proceedings of the Fourth Annual International Conference on Computational Molecular Biology (Tokyo, Apr. 2000), pp. 245-253.

Preparata, F., Frieze, A., and Upfal, E. On the power of universal bases in sequencing by hybridization. In Proceedings of the Third Annual International Conference on Computational Molecular Biology (Lyon, France, Apr. 1999), pp. 295-301.

Delcher et al., "Alignment of whole genomes", Nucleic Acids Research, 1999, vol. 27, No. 11, pp. 2369-2376.

Califano, A., et al., "FLASH: Fast Look-up Algorithm for String Homology", IBM T.J. Watson Research Center, May 4, 1998.

Buhler, Jeremy, "Efficient Large-Scale Sequence Comparison by Locality-Sensitive Hashing", Bioinformatics 17(5), pp. 419-428, 2001.

Burkhardt, et al., "q-gram Based Database Searching Using a Suffix Array (QUASAR)", 3rd Annual International Conference on Computational biology, 7 pgs, 1999.

Altschul, S., et al. "Basic Local Alignment Search Tool", J. Mol. Biol., (1990) 215, pp. 403-410.

Kent, Internet Article, "The Bast-like Alignment Tool", www.genome.org/cgi/content/full/12/4/656, 2003, 20 pgs.

* cited by examiner

*Primary Examiner* — Eric S DeJong

(74) *Attorney, Agent, or Firm* — Norton Rose Fulbright Canada LLP

(57) ABSTRACT

An area of research in the field of bioinformatics deals with the identification of similarities within one, or between two DNA sequences. Current techniques are quite slow and many matches are missed. The invention provides a faster and more sensitive solution, by using "optimized spaced seeds" to perform these biological sequence homology searches. Various techniques are shown for identifying seeds which are optimized to improve the sensitivity or speed of the searching. In the preferred embodiment, optimized spaced seeds are determined by the parameters of the search and independent of the actual databases being searched (for example, using the length and weight of the spaced seed, as well as the probability of a hit in a similar region). Thus, these optimized seeds can be stored in libraries which are accessed as required.

9 Claims, 13 Drawing Sheets

30
32
36
48
I/O
40
CPU
42
MEMORY
44
46
MODEM
38
34

START
GENERATE A LIBRARY OF OPTIMIZED SEED MODELS
100
FOR EACH SEARCH TASK
102
DONE
DONE
NEXT SEARCH
CHOOSE AN OPTIMISED SEED MODEL
104
FAIL
TRY TO GENERATE A NEW HIT
106
SUCCESS
EXTEND HIT TO AN HSP
108
IS HSP SCORE > THRESHOLD?
110
NO
YES
GAP EXTENSION TO GENERATE AN ALIGNMENT
112
IS ALIGNMENT SCORE > THRESHOLD?
114
NO
YES
OUTPUT ALIGNMENT
116

START
INPUT: L, M, s AND p
120
CALCULATE B1
124
LET f [i, b] = 0 FOR ALL 0 < i < M AND STRINGS b, THAT ARE ELEMENTS OF B1
126
DONE
FOR i = M TO L
128
NEXT i
TAKE SUCCESSIVE b FROM B, FROM LONGEST TO SHORTEST
130
DONE
NEXT b
IF |b| = M THEN f [i, b] = 1, ELSE, FIND THE SMALLEST J ≥ 0, WHERE 0b >> J IS AN ELEMENT OF SET b1; AND LET f [i, b] = (1 - p) x f [i - j, 0b >> j] + p x f [i, 1b]
132
OUTPUT f [L, ϵ}
134
DONE

START
EXTEND HIT TO THE LEFT
160
EXTEND HIT TO THE RIGHT
162
IS
SCORE ≥ THRESHOLD?
164
NO
YES
GAP EXTENSION
166
ALL HITS CHECKED?
168
NO
NEXT HIT
169
YES
DONE

METHOD AND SYSTEM FOR FASTER AND MORE SENSITIVE HOMOLOGY SEARCHING

CROSS-REFERENCE TO RELATED APPLICATIONS

The present application is a divisional of U.S. patent application Ser. No. 10/236,339 filed Sep. 6, 2002, claiming priority to U.S. Provisional Patent Application No. 60/338,480 filed Dec. 3, 2001, and Canadian Patent Application No. 2,357,263 filed Sep. 7, 2001.

The present invention relates generally to biotechnology and information technology, and in particular, to a subfield known as bioinformatics. A specific aspect of the invention lies in the provision of a new method and system for identifying similarities within one, or between two DNA sequences more quickly and with greater sensitivity than known techniques.

BACKGROUND OF THE INVENTION

The field of bioinformatics lies at the intersection of computer science and molecular biology. Among other things, it deals with methods of processing and analysing genomic and proteomic information.

For the first time in our natural history, we have access to complete genomic sequences of *H. sapiens, C. elegans, A. thaliana, D. melanogaster, M. musculus, S. pombe, S. cerevisiae*, rice, dozens of prokaryote genomes, and hundreds of virus genomes (the initial sequences of the human genome, for example, may be found at the following references: *International Human Genome Sequencing Consortium, Initial sequencing and analysis of the human genome*, Nature 409, pp. 860-921, 2001, and J. C. Venter et al., *The sequence of the human genome*, Science 291, p. 1304, 2001). However, the potential of this enormous and exponentially growing wealth of information will be wasted if proper tools to mine it are not developed.

One class of crucial tools is homology search programs for finding similar regions within one or between two DNA sequences. Genomics studies routinely depend on such homology search tools. It is not surprising that many algorithms and programs have therefore been developed for the task, including the following:

- FASTA; see D. J. Lipman, W. R. Pearson, *Rapid and sensitive protein similarity searches*, Science 227, pp. 1435-1441 (1985);
- SIM; see X. Huang and W. Miller, *A Time-efficient, Linear-Space Local Similarity Algorithm*, Advances in Applied Mathematics, 12, pp. 337-357 (1991);
- the Blast (Basic Local Alignment Search Tool) described by S. F. Altschul, W. Gish, W. Miller, E. Myers and D. J. Lipman, *Basic local alignment search tool*, J. Mol. Biol., 215, 403-410 (1990); and the family of related tools that it spawned, including WU-Blast, Psi-Blast, MegaBlast and BL2SEQ;
- SENSEI; see a description by D. States on the SENSEI Web site at: http://stateslab.wustl.edu/software/sensei/;
- MUMmer; see A. L. Delcher, S. Kasif, R. D. Fleischmann, J. Peterson, O. White, and S. L. Salzberg, *Alignment of whole genomes*, Nucleic Acids Research, 27:11, 2369-2376 (1999);
- QUASAR; see S. Burkhardt, A. Crauser, H-P. Lenhof, E. Rivals, P. Ferragina and M. Vingron, *q-gram based database searching using a suffix array,* 3rd Ann. International Conference on Computational Molecular Biology, Lyon 11-14, April 1999; and
- REPuter; see S. Kurtz and C. Schleiermacher, *REPuter—Fast computation of maximal repeats in complete genomes*; Bioinformatics, 15:5, 426-427 (1999).

These existing search tools are far from adequate to handle the amount of biological sequences currently available. For example, the best program currently available (Blast) would take almost 19 CPU-years to compare the human genome and the mouse genome on a modern personal computer. Other examples of the excessive times these routines require to perform a search are presented in Table 1 and Table 2 included hereinafter. Despite the slowness, Blast's sensitivity is not great, that is, it would miss many similarities for the reasons explained hereinafter.

Clearly then, more sensitive and more efficient homology search tools are urgently needed.

Given two long DNA sequences, exhaustively comparing all bases against all bases is well-known to be too slow. However, two approaches have been used to improve the situation. The first is exemplified by Blast, which is used routinely by thousands of scientists. In this approach a match of two short substrings of the two long DNA sequences is called a "seed match", or a "hit". The approach finds all the hits and tries to extend the hits into longer alignments. However, when comparing two very long sequences, FASTA, SIM, Blastn (BL2SEQ), WU-Blast, and Psi-Blast run very slowly and need large amounts of memory. SENSEI and MegaBlast try to improve the running speed by sacrificing quality. MegaBlast, at its large seed length of 28, outputs low quality alignments. SENSEI does not even do gapped alignments (a gap is a series of spaces inserted to one of the two sequences; in order to obtain a good alignment, very often several gaps need to be inserted into the two sequences). Thus, it is desirable to improve the quality of hits, and reduce the running time for an analysis.

Programs that depend on the strategy of finding short seed matches which are then extended, will be referred to herein as "Blast-type" programs. Blast-type programs exhibit a tradeoff between sensitivity and speed according to the chosen seed size. That is, increasing seed size reduces the time it takes to process a search, but it also decreases sensitivity (which means that it misses sequence matches).

Another approach, exemplified by MUMmer, QUASAR and REPuter, is based on suffix trees. Suffix trees are standard data structures in Computer Science. A suffix tree is used to build an index table for a target string in order to find the exact match of a query string efficiently. The technique of finding sequence matches using suffix trees suffers from two major problems:

1. they are meant to deal with precise matches and are limited to comparison of highly similar sequences. They are very awkward in handling mismatches because the suffix tree is not designed to allow for mismatches in the sequence; and
2. they have an intrinsic large space requirement.

Due to these obstacles, it is not expected that this approach will lead to practical homology software with quality comparable to Blast-type algorithms.

In similarity searching, not only exact matches of short strings can be used as seeds (as short matches can be used to find longer alignments). A number of techniques using other kind of matches as seeds have been proposed, but all have serious shortcomings. For example:

1. locally-sensitive hashing (LSH) described by P. Indyk and R. Motwani in: *Approximate nearest neighbors: towards removing the curse of dimensionality*, Proc. 30th Ann ACM Symp. Theory Comput., 1998, Dallas, Tex., has been applied to ungapped homology search in J. Buhler, *Efficient large-scale sequence comparison by locality-sensitive hashing,* Bioinformatics, 17, 419-428 (2001). LSH is a random hashing/projection technique unsuitable for gapped homologies.

In Buhler, in each of hundreds of iterations, a newly chosen random hash function is applied to every region of a fixed size (of about 100), and regions mapping to the same value are fully compared. Similar overlapping regions are then merged into ungapped alignments. However, a long ungapped alignment can only be found if the regions found to be similar cover its whole length;

2. earlier than Buhler, a similar idea had been applied in Flash (see A. Califano and I. Rigoutsos, *FLASH: fast look-up algorithm for string homology*, Tech. Rep., IBM T. J. Watson Research Center, 1995), which used shorter regions. Both approaches focused on covering a homology entirely with hits, instead of doing hit-extension in Blast style. The Flash authors tried to use many seeds to cover a region, using "randomly" generated tuples. Flash is aimed at fully covering an ungapped region which is less efficient than using Blast-style hit extensions;
3. in two other references, the proposal is made to use periodically spaced probes in sequencing by hybridization studies (see F. P. Preparata, A. M. Fieze, and E. Upfal, *On the power of universal bases in sequencing by hybridization*, RECOMB, 1999, pp. 295-301 and F. P. Preparata and E. Upfal, *Sequencing-by-hybridization at the information-theory bound: an optimal algorithm*, RECOMB, 2000, pp. 245-253). However, all of their seeds have a predetermined pattern, $1^s(0^{s-1}1)^u$ for some s and u (where $1^s$ means that "s" consecutive characters must match, and $0^{s-1}$ means that "s−1" consecutive characters do not match, etc.).

Clearly, these predetermined seed patterns are not optimal for general homology searches. Thus, given an arbitrary homology problem, this methodology will offer no improvement in processing speed or performance;
4. several programs, including SENSEI, Exonerate, and Blastn, may allow a mismatch in consecutive length k-seed matches. This has the same performance as the use of k seeds with pattern $1^{i-1}01^{k-i}$. However, because the k seeds are quite dependant to each other, the use of them together will slow down the search significantly, yet provide very limited improvement on the sensitivity;
5. another program called BLAT developed by Jim Kent uses seeds with predetermined patterns such as 110110110, with 0's in every third position (i.e we do not care whether there is a match in the 0 locations). This particular pattern is used in coding region analysis where the third position is simply not as important as the first two.

In other words, Kent is merely teaching that the seed be designed to search for what the user wishes to find. Kent's teachings are therefore of no assistance in solving the general search problem, where the user does not know where the mismatches will lie (and, for the sake of the general search problem, does not care where the mismatches lie). Thus, this approach is basically the same as the consecutive seed scheme of Blast and it does not optimize the probability of a hit.

Thus, all of the above attempts at handling local gapped alignments employ either random hash functions, and/or multiple predetermined patterns. As explained above, they cannot offer any improvement in both the sensitivity and the speed of the general homology search.

There is therefore a need for means of improving homology searching, provided with consideration for the problems outlined above.

SUMMARY OF THE INVENTION

It is therefore an object of the invention to provide a method and system which obviates or mitigates at least one of the disadvantages described above.

The invention resolves the problems with modern homology search software by:

1. providing a new seed scheme that increases sensitivity without increasing search time; and
2. providing a new, efficient method to extend seed matches to build gapped alignments.

One aspect of the invention is broadly defined as a method of performing biological sequence homology searches comprising the steps of: generating one or more optimized spaced seeds, by identifying optimized spaced seeds with a high likelihood of having hits in the similar regions; and performing a Blast-type search using the one or more optimized spaced seeds; thereby improving speed and sensitivity of the homology search.

BRIEF DESCRIPTION OF THE DRAWINGS

These and other features of the invention will become more apparent from the following description in which reference is made to the appended drawings in which.

DESCRIPTION OF THE INVENTION

Figure 1:
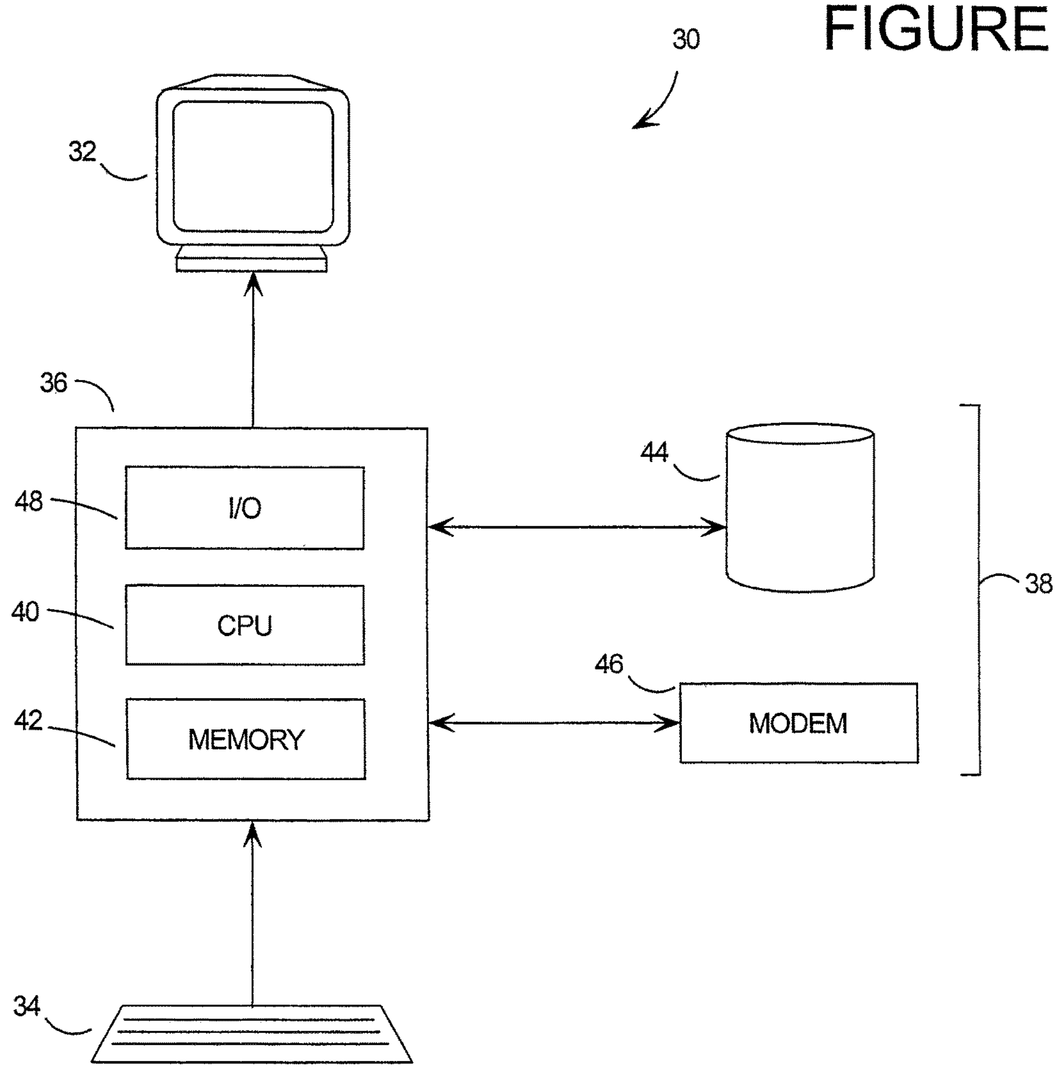
FIG. 1 presents a block diagram of a personal computer (PC) which may be used in an embodiment of the invention.

The invention provides a novel seed model that simultaneously increases sensitivity and search speed. The invention also introduces new methods of building gapped alignments.

The preferred embodiment of the invention has been implemented in a portable Java program called "PatternHunter". At default levels of sensitivity comparable to Blastn, it is able to find homologies between sequences as large as human chromosomes, in mere hours on a desktop computer. This by far exceeds the power and quality of competing programs.

On a modern desktop, PatternHunter's running time ranges from seconds for prokaryotic genomes, to minutes for arabidopsis chromosomes, to hours for human chromosomes, with very modest memory use, and at provably higher sensitivity than the default Blastn.

One particular application of the invention is in comparative genomics where large genomes or chromosomes such as the human genome need to be compared. Another application is cross species comparison to assist the sequence assembly in shotgun sequencing. For example, a project was recently undertaken to find all the homologies between 16 million reads (of about 500 base pairs each) of the mouse genome and the 3 gigabases of the human genome. It took an embodiment of the invention 20 CPU-days to finish this task, while the best Blast program would have taken almost 19 CPU-years.

Before describing the invention, a review of the notation and framework for the discussion will be presented.

First, if not otherwise mentioned, a sequence such as a DNA sequence, refers to a string of characters from the alphabet {A, C, G, T} (this is the alphabet used for DNA sequences; the alphabet for protein sequences has 20 letters). For example: ATGACGTTA is a sequence of 9 characters. Each of A, C, G, T is called a nucleotide, or a base, in molecular biology.

The homology search problem may be described as follows:

Input: two sequences. One of these is often a query, and the other is often a target database. Both sequences could be very long; as long as billions of bases.

A typical example is the comparison of the mouse genome and the human genome, where both sequences are about 3 billion bases. Another example would be searching a query sequence in GenBank, where the query sequence might be as short as a hundred base pairs while GenBank contains billions of DNA bases.

Goal: find "similar" regions between the two sequences with high scores. The scoring scheme is usually defined as input parameters by the users. One such scoring scheme used in an embodiment of the invention is: reward a match with 1, penalize a mismatch with −1, open gap −5, and gap extension −1 (other scoring schemes can also be used). Finding the match of two similar regions is formally called the local alignment of the two similar regions.

For example, if we assume that one sequence contains a substring AATGAGATAGACCTTTA, and another sequence contains a substring AATTATAGTCCTTTA, then these two substrings can be aligned as:

```
AATGAGATAGACCTTTA
|||  |  ||| ||||||
AATTA--TAGTCCTTTA
```

where the two spaces "--" represent a gap. A vertical bar represents a match, and the absence of a vertical bar implies a mismatch. According to the above scoring scheme, this alignment has a score of 13−2−5−1=5.

Second, the method of the invention may be applied on virtually any computer or microprocessor-based system. A server, minicomputer or mainframe on a local area network or connected to the Internet, could, for example execute the algorithm and pass the results of any queries back to the user. An exemplary system on which the invention may be implemented, is presented as a block diagram in FIG. 1.

This computer system 30 includes a display 32, keyboard 34, computer 36 and external devices 38. The computer 36 may contain one or more processors or microprocessors, such as a central processing unit (CPU) 40. The CPU 40 performs arithmetic calculations and control functions to execute software stored in an internal memory 42, preferably random access memory (RAM) and/or read only memory (ROM), and possibly additional memory 44. The additional memory 44 may include, for example, mass memory storage, hard disk drives, floppy disk drives, magnetic tape drives, compact disk drives, program cartridges and cartridge interfaces such as those found in video game devices, removable memory chips such as EPROM or PROM, or similar storage media as known in the art. This additional memory 44 may be physically internal to the computer 36, or external as shown in FIG. 1.

The computer system 30 will also generally include a communications interface 46 which allows software and data to be transferred between the computer system 30 and external systems. Examples of communications interface 46 can include a modem, a network interface such as an Ethernet card, or a serial or parallel communications port. Software and data transferred via communications interface 46 are in the form of signals which can be electronic, electromagnetic, optical or other signals capable of being received by communications interface 46. Multiple interfaces, of course, can be provided on a single computer system 30.

Input and output to and from the computer 36 is administered by the input/output (I/O) interface 48. This I/O interface 48 administers control of the display 32, keyboard 34, external devices 38 and other such components of the computer system 30.

The invention is described in these terms for convenience purposes only. It would be clear to one skilled in the art that the invention may be applied to other computer or control systems 30.

The common practice of Blast-type homology searches use k consecutive letters in the two input sequences as seeds (default k=11 in Blastn, k=8 in SENSEI, and k=28 in MegaBlast). If two seeds at locations in the two sequences match, then the neighbourhood of these two locations might be similar. Hence, these two locations are further inspected by extending the seed match to the left and to the right to see whether a long alignment can be built. Often, the match of two seeds is also referred as a hit.

The dilemma for a Blast type of search is that large seeds lose sensitivity because two similar but not identical sequences may not contain a large seed match and therefore cannot be detected; whereas small seeds create too many random seed matches which slow down the computation dramatically.

The invention introduces a new method that yields a higher probability of a hit in a homologous region, while having a lower expected number of random hits, thus shifting this dilemma. This allows homology searching to have higher sensitivity while increasing speed at the same time.

The invention does this by utilizing optimized non-consecutive, or 'spaced' k letters as seeds. A seed model in the invention is the relative positions of the k letters, and k is called the weight of the model. For convenience, a seed model is denoted by a 0-1 string, where letter 1s indicate the positions that need to be matched. For example, the model 1101 indicates that the match of two substrings is called a seed match (or a hit) if and only if the first, second and fourth positions of the two substrings are matched. In the invention, seed models are optimized for maximum sensitivity, and optimized (or nearly optimized) seed models are used to generate hits. Then, the hits are extended to generate alignments.

It is noteworthy that the traditional consecutive seed models can be represented as strings with only 1s. Surprisingly, it can be shown mathematically that the traditional consecutive seed models are the worst seed models with the lowest sensitivity.

Figure 2:
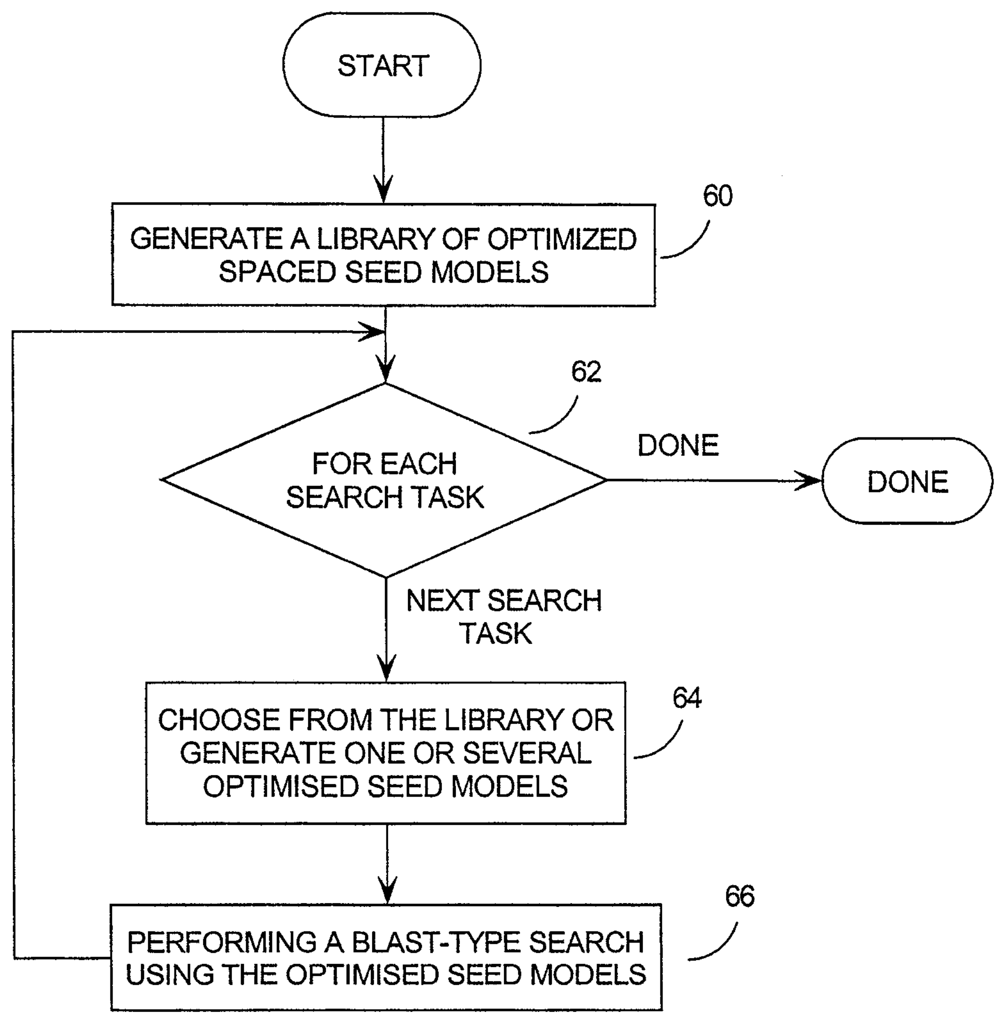
FIG. 2 presents a flow chart of a broad embodiment of the invention.

The invention can be generally represented in the flow chart of FIG. 2. Briefly, this figure presents a method of performing biological sequence homology searches. The invention can be applied to any manner of biological sequence including the DNA and amino acid sequences described herein. These sequences being compared are generally referred to herein as a "query" sequence and a "target" sequence, as it is a common research task to determine whether a short sequence (the query) exists in a complete genome (the target sequence). The method of the invention, of course, can be applied to any pairing of sequences; short or long, fragment or complete genome.

The method begins with step 60 in which a library of optimized spaced seed models are generated. The method of generating optimized spaced seed models is described in greater detail hereinafter, but in short, the optimized spaced seed models are generated by considering the likelihood that proposed seed models will have hits in the similar regions. Typically we do not know all the pairs of similar regions before the search is done. However, we can know some statistical properties of all the pairs of similar regions. Let (a,b) be a random pair of similar regions. That is, whether a and b match at a certain position is a random event. The probability that a and b match at each position is assigned either by the users or by a statistical analysis of the query and database sequences. (In the latter case, the random pair of similar regions can be considered as a profile of all the similar regions; in the former case, the users aim to find the seed models that are optimized to find the similar regions that can be profiled by the random pair.) Then, the spaced seed models are tested against such a random pair of similar regions. Those spaced seeds that have the highest likelihood of having hits in such a random pair of similar regions, will also have a high likelihood to hit more similar regions in the search than any other seed.

These optimized spaced seeds can be generated independently of the query and target databases, thus, optimized spaced seeds could be calculated ahead of time. A library of optimized spaced seeds could be generated by a software supplier and made available to users, the library of optimized spaced seeds being indexed by the search parameters. Thus, the user would not have to invest time in generating new optimized spaced seeds each time a query is made. As well, of course, users could generate their own optimized spaced seeds corresponding to their own search parameters.

The technique for developing optimized seed models is described in greater detail hereinafter. These seed models may be generated to optimize the sensitivity without generating more random hits, and/or optimising the speed of the search; these two parameters being closely intertwined.

The next step in FIG. 2, is then to respond to a given search task being requested at step 62, by choosing one or more of the seed models at step 64. These seed models are used to perform a Blast-type similarity search at step 66, yielding the hits between the query and target databases. A "Blast-type" search is one in which short seed matches are found, which are then extended. The method of the invention could be applied to other searching strategies, but is most effective in Blast-type searches.

The routine then loops back to step 62 so that additional searches can be performed. When it is determined at step 62 that all search tasks have been performed, the routine exits.

Note that the essence of the invention may be taken by performing different steps than those described above with respect to FIG. 2.

The invention of FIG. 2 addresses the problems in the art. The seemingly simple change to the seeds being used has a surprisingly large effect on sensitivity. An appropriately chosen seed model can have a significantly higher probability of having at least one hit in a homologous region, compared to Blast's consecutive seed model, while having a lower expected number of hits.

Figure 3:
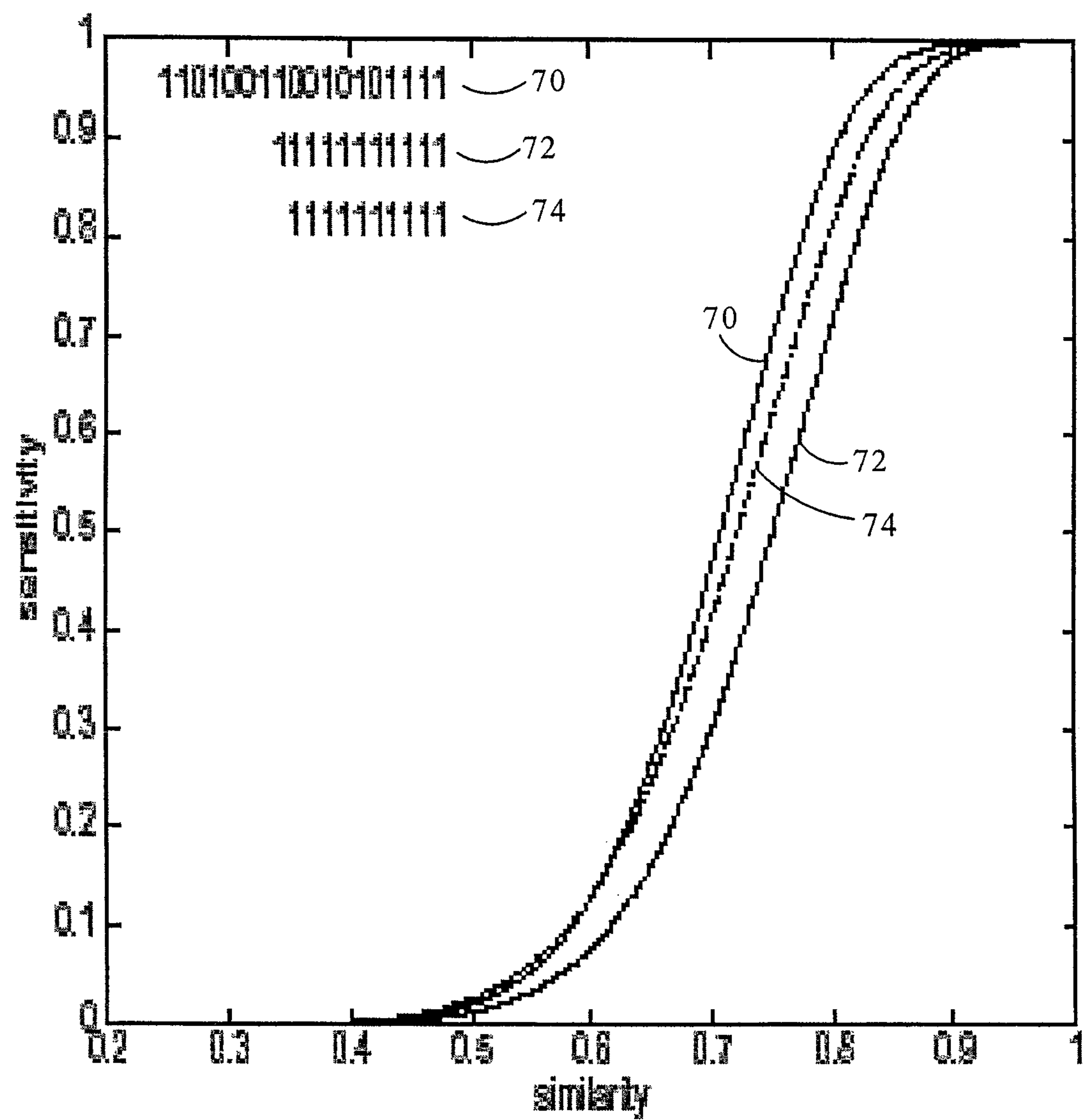
FIG. 3 presents a graph comparing 1 hit performance of a weight 11 spaced seed model versus weight 11 and 10 consecutive seed models.

For example, in a match of length 64 with 70% identity, Blasts consecutive weight 11 model (curve 70 in FIG. 3) has a 0.30 probability of having at least one hit in the range, while a non-consecutive model of the same weight (curve 72) has a 0.466 probability of getting a hit (note that seed in FIG. 3 is not even the optimal seed, the optimal seed is 111010011001010111 for that case). As well, the expected number of hits in that region by the Blast consecutive model is 1.07, while the non-consecutive model expects 0.93 hits, about 14% less. Thus, the method of the invention will take less time to discover more useful hits which may be extended to longer matches.

Figure 4:
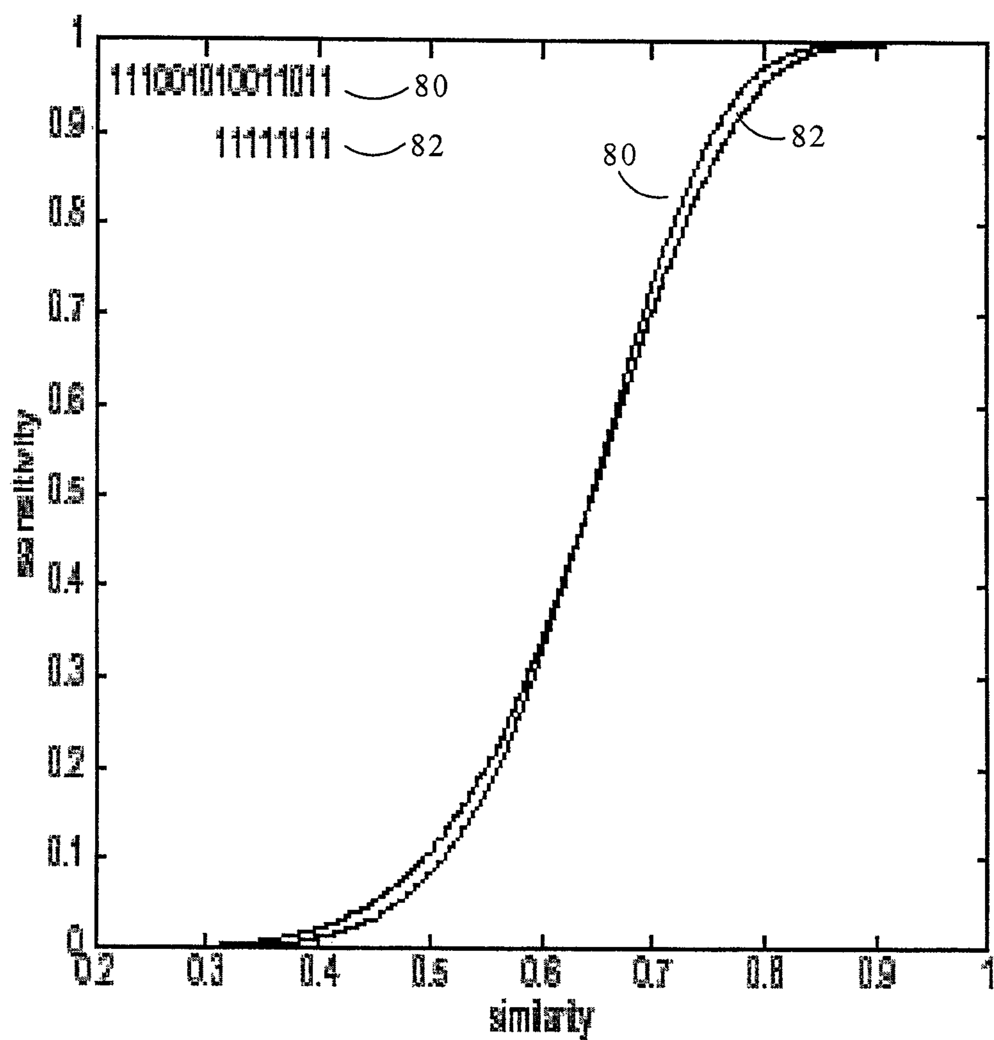
FIG. 4 presents a graph comparing 1 hit performance of weight 8 consecutive model versus weight 9 non-consecutive model.
Figure 5:
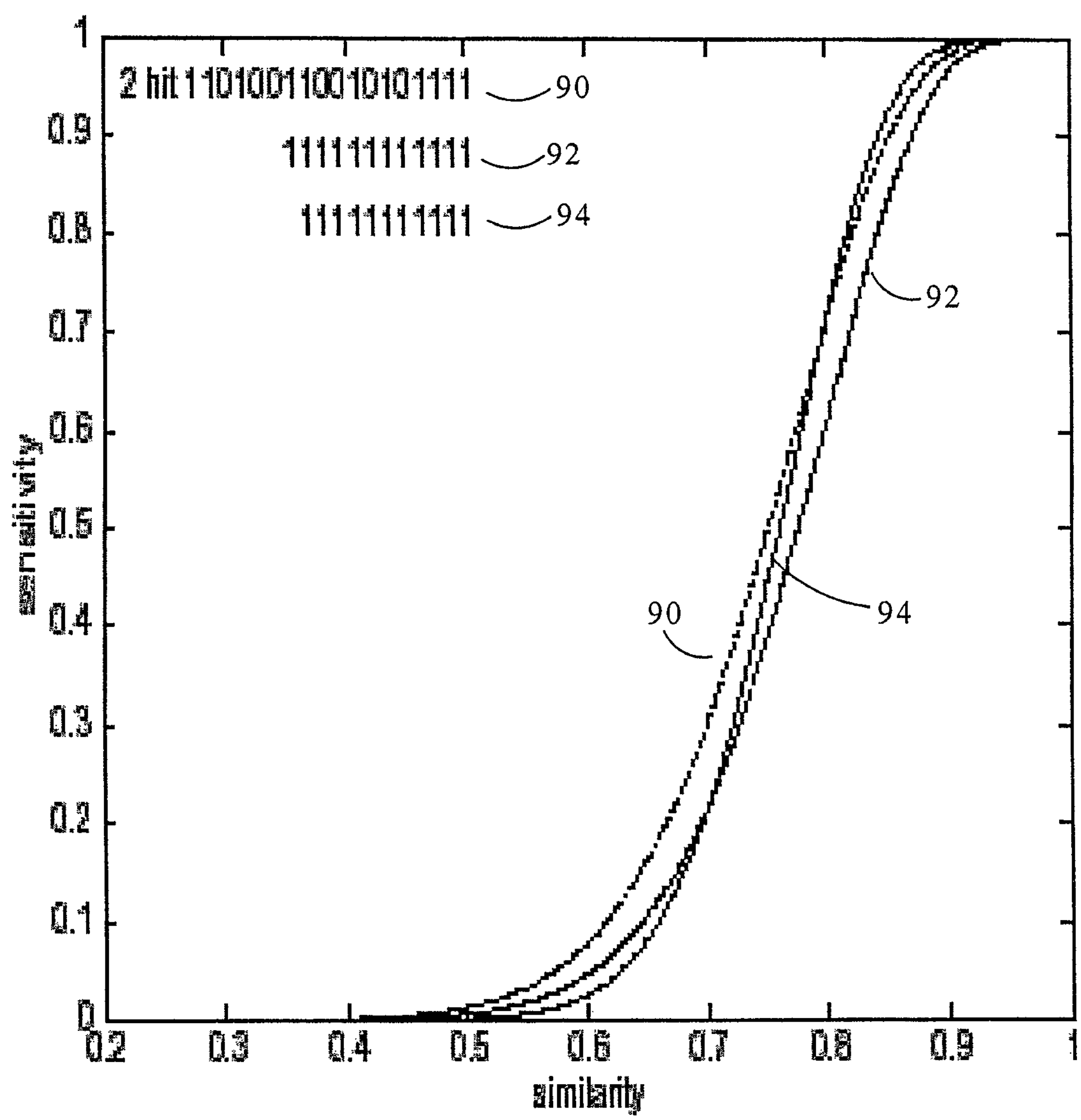
FIG. 5 presents a graph comparing 2-hit performance of weight 11 spaced model versus single hit weight 11 and 12 consecutive models.

To evaluate a seed model, the invention computes the probability of generating a hit in a fixed length region of given similarity. FIGS. 3, 4 and 5 compare non-consecutive models with Blast's consecutive models. For each similarity percentage shown on the x-axis, the percentage of length-64 regions acquiring at least 1 hit is plotted on the y-axis as the sensitivity at that similarity level in FIG. 3.

Similarly, FIG. 4 compares the sensitivity of SENSEI using a default seed size of 8 (curve 82), with that of a spaced weight 9 model in a manner of the invention (curve 80).

Also, FIGS. 3 and 4 show that we can use an optimized (or nearly optimized) spaced model of weight 9 (curve 80 in FIG. 4) to replace a consecutive weight 8 (curve 82 in FIG. 4) model, gaining sensitivity above 64% similarity, or use a weight 11 (curve 70 in FIG. 3) spaced model to replace a weight 10 consecutive model (curve 74 in FIG. 3) gaining sensitivity above 60%. A similar phenomenon occurs for all weights greater than four. That is, an optimized spaced model with weight $W>4$ can gain better sensitivity than a consecutive seed model with weight $W-1$.

Theoretically, the expected number of hits of a weight W, length M model within a length L region of similarity $0\le p\le 1$ can be easily calculated as (L−M+1) $p^W$, since there are (L−M+1) possible positions of fitting the model within the region, each having probability $p^W$ of a match.

By the above argument, for a region length of 64, Blast seed of length 11, the expected number of hits of a non-consecutive seed of length 18 and weight 11 is about 14% lower than Blast, speeding up hit processing by the same amount (to some extent, this is offset by the longer time needed to calculate an optimal spaced seed). On the other hand, observing FIG. 3, the spaced model always has a significantly higher probability of at least one hit, when the similarity level is reasonably high.

Following the previous argument, the weight W spaced model has only a fraction p of the hits of the weight (W−1) consecutive model over all p similarity regions. In the admittedly artificial case we assume all pairs of similar regions have 60% similarity and length 64, and two randomly picked regions have average 25% similarity (because there are four letters). Then in the pairs of the similar regions, the weight Wspaced model has only 60% of the hits of the equally sensitive weight W−1 consecutive model. In the random regions, the weight W spaced model has only a quarter of the hits of the equally or less sensitive weight W−1 consecutive model. Thus, optimized spaced seeds can be used to gain selectivity (produce less hits), and therefore, improve the search speed.

As described in the Background above, others have attempted to improve homology searching techniques known and used in the art. However, none of these, and no one else, has ever proposed the use of deterministic optimized spaced seeds in homology searching, which are optimized to maximize the probability of a hit in a homologous region. As well, no one has proposed the use of such optimized spaced seeds in Blast-type homology searching with gapped local alignments. In fact, no one has proposed the use of approximately optimized, or reasonable spaced seeds which provide a higher probability of hits, for Blast-style homology searching with gapped local alignments.

Double, Triple, or k Hits Using Optimized Spaced Model, AND and OR Methods

In order to improve selectivity, this invention uses a k-hit method (for k=2, 3 or small integer) with the optimized (or nearly optimized) spaced model. That is, hits of the spaced model are only extended if k of them occur close together on a single diagonal (a description of how "diagonals" are used in given hereinafter).

Double hits have been used in the art, in limited ways. The current 1.4 version of Blast, for example, triggers an extension if two disjoint hits are found on the same diagonal within a certain distance of one another. The increased selectivity more than offsets the loss in sensitivity, so that it can use a smaller weight model and still generate fewer extensions than an equally sensitive 1-hit model of larger weight.

The combined usage of k-hits with the optimized spaced models however, is particularly advantageous. With optimized spaced seeds, hits are no longer required to be disjoint in order to gain a lot of sensitivity. FIG. 5 compares the sensitivity of a double hit, spaced weight 11 model (curve 90) against single hit, weight 11 and 12 consecutive models (curves 94 and 92 respectively). Clearly, the double hit model generates far fewer random hits than the other models, as well as offering higher levels of sensitivity for regions with similarity levels between 0.45 and 0.75.

In order to improve sensitivity, the invention uses multiple spaced models to find all the homologies that any of the models can find. The set of models is chosen to maximize the probability that at least one of the models hits a homologous region. This gives a better sensitivity-speed tradeoff than the alternative of allowing 1 mismatch. For a weight 11 model, the latter method of allowing 1 mismatch is equivalent to using 11 highly dependent models each of weight 10—its gain of sensitivity is offset by a major slow down. The same increase in sensitivity can be obtained with only a few independent spaced models.

The invention is different from the method of randomly generating hits to cover homologous regions in the following ways:

1. the spaced seed is designed specifically for the purpose of finding a seed match and then relying on both ungapped and gapped extensions to cover the whole of a homology. This has not been done before;
2. in the invention, the spaced model is optimized for sensitivity. This has not been done before; and
3. even randomly generated spaced models have reasonable behaviour when used in the same manner as in item 1. This has not been observed or done before.

In summary, the invention includes the use of one or more optimized (or approximately optimized) seed models in single or multiple-hit mode. Multiple hits increase search speed at the cost of sensitivity and multiple models increase sensitivity at the cost of speed.

Method Steps of an Exemplary Embodiment of the Invention

An exemplary embodiment of the invention was implemented in Java using the spaced seed model and various algorithmic improvements using advanced data structures. Its key steps and inventions are described in the following.

Figure 6:
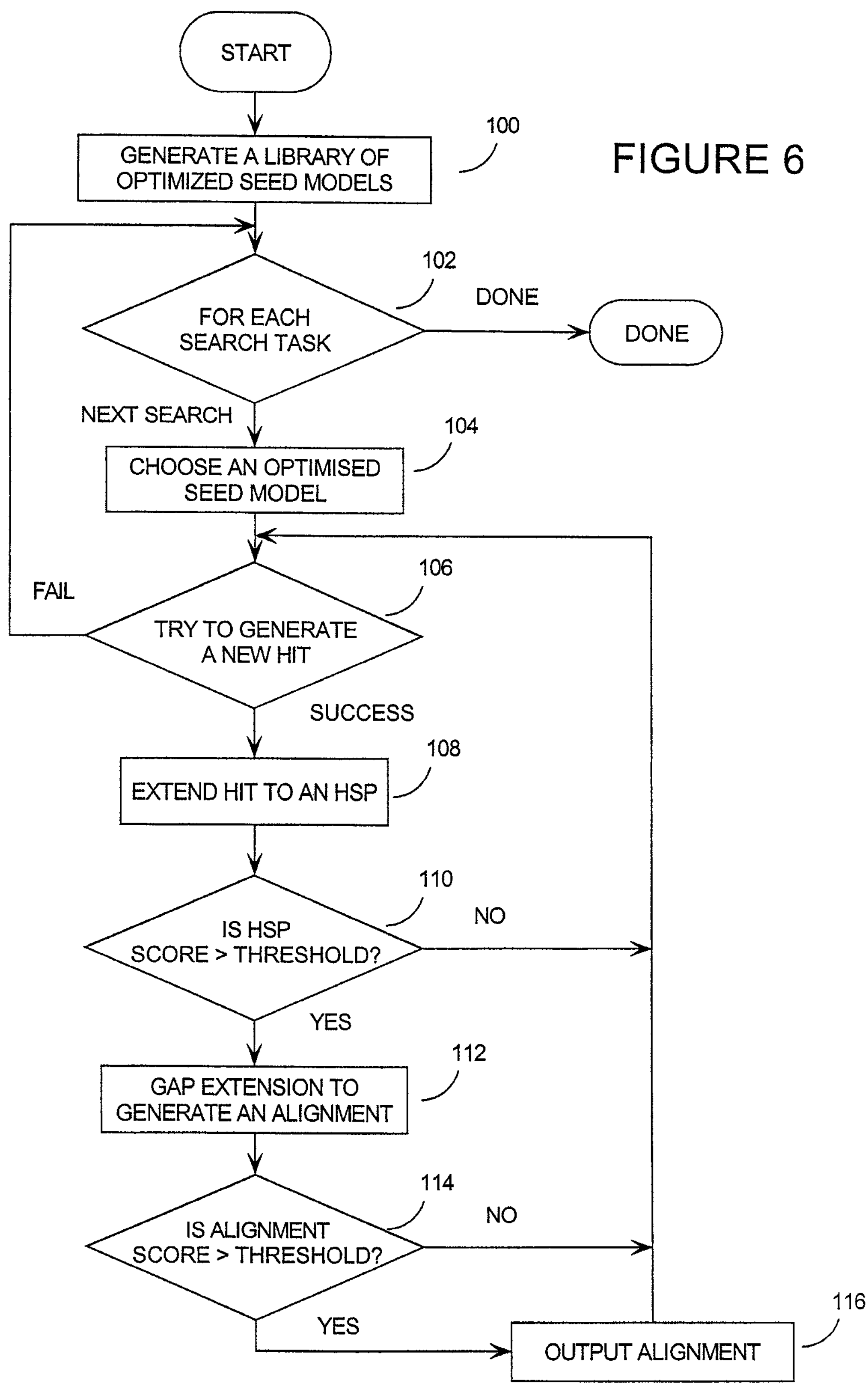
FIG. 6 presents a flow chart of an overview of an exemplary embodiment of the invention.

An overview of this methodology is presented in the flow chart of FIG. 6. The methodology first calculates a library of optimal spaced seeds ahead of time at step 100. Then for each search task per step 102, it performs the following steps:

1. choosing an optimal spaced seed at step 104;
2. trying to generate a new hit at step 106. If this search fails, then control returns to step 102, otherwise the process continues;
3. extending a successful hit into an HSP (Highscoring Segment Pair) at step 108 (HSPs are known in the art, but are described in greater detail hereinafter);
4. if the score of a generated HSP does not meet a minimal level at step 110, then control returns to step 106 so that another attempt can be made to find a suitable hit. Otherwise, processing continues to step 112;
5. at step 112, gap extension is performed to extend the HSP into an alignment;
6. if it is determined at step 114 that the score of this alignment meets a minimal threshold then the alignment is considered acceptable, and it is output at step 116. Otherwise, control returns to step 106.

Note that steps 106 through 116 can be performed in a slightly different order than that shown in FIG. 6. For example, all the hits can be generated before any of them are extended HSPs; and/or all the HSPs can be generated before any of them are gap extended to alignments.

These steps are described in more detail with respect to FIGS. 7 through 10.

The first part of the process is to calculate optimal seeds. A reasonably fast method for finding optimal seeds is presented in FIG. 7. In the preferred embodiment, the approach is to consider all possible spaced seed models of a certain weight and length. A calculation is done to determine the likelihood that each of these proposed seed models will find hits in a random pair of similar regions. Clearly, the match of such pair of regions can be represented by a random 0-1 string, where, a letter in the string is 1 if and only if the two regions match at the corresponding position. Therefore, the probability that the i-th letter of the string is 1 is equal to the probability that the pair of regions match at the i-th position. In this exemplary embodiment of the invention, we simply assume that the pair of the similar regions match at each position independently with probability p. Thus, the spaced optimized seed models will vary with the parameters of this analysis, rather than with the actual data in the query or target sequences.

Given seed model length M, weight W, homology region of length L, and homology level p, this method computes, for each seed model of length M and weight W, the probability of having a hit in a homology region of length L and homology level p. This is accomplished by using a dynamic programming method; then the method chooses the most sensitive seeds.

Let R be a random 0-1 string of length L. Each bit independently is 1 with probability p. Recall that we use R to represent a homologous region of length L with homology level p: a match in the region is represented as a 1 in R, and a mismatch in the region is represented as a 0 in R; and there are about p*100 percent 1's in the region. Let s be a seed model with weight W, length M. That is, s contains W bits with a value of 1, and (M−W) bits with a value of 0.

A seed match of s at location i in R means putting seed model s starting at the i-th position in R, all 1's in s match with 1's in R. Let $A_i$ be the event that seed s has a seed match at location i in R, $0 \le i \le L-M$. Our goal is an algorithm to compute the probability that s hits R, i.e., $$P\left(\bigcup_{j=0}^{L-M} A_j\right) \cdot \left(\bigcup_{j=0}^{L-M} A_j\right.$$

means at least one of $A_j$ happens.)

Let $b=b_0b_1 \ldots b_{i-1}$ be a binary string of length L. For any $M \le i \le L$ and any b such that $I=|b| \le M$, we use f(i, b) to denote the probability that s hits the length i prefix of R that ends with b:

$$f(i, b) = P\left(\left(\bigcup_{j=0}^{i-M} A_j \mid R[i-I, \ldots, i-1] = b\right)\right).$$

Clearly, $$P\left(\left(\bigcup_{j=0}^{i-M} A_j\right) = f(L, \varepsilon),\right.$$

where ϵ denotes the empty string. The idea of the dynamic programming approach is to compute all f (i, b) gradually for i from M to L, and for all b in a suitably chosen small subset $B_1$ of $B=\{0, 1\}^{\le M}$.

$B_1$ will contain all b "compatible" with s, in the sense that $A_{i-M} \cap (R[i-I, \ldots, i-1]=b) \ne \emptyset$ (that is, the two events $A_{i-M}$ and $R[i-I, \ldots, i-1]=b$ can happen together.). The size of $B_1$ is bounded by $M2^{M-W}$, since for each length $I \le M$, at most M−W bit positions are not constrained.

For $b \in B_0 = B \setminus B_1$, (where $B \setminus B_1$ means the set of all members of B with all members of $B_1$ removed), $A_{i-M} \cap (R[i-I, \ldots, i-1]=b)=\emptyset$, so in that case, $P(A_{i-M} \mid R[i-I, \ldots, i-1]=b)=0$. Consequently, $$f(i, b)=f(i-1, b>>1)$$

where b>>j denotes the binary string $b_0\, b_1 \ldots b_{i-1-j}$.

If $b \in B_1$ and $|b|=M$ then $A_{i-M} \supset \{R[i-M, \ldots, i-1]=b\}$ (that is, $A_{i-M}$ happens whenever $R[i-M, \ldots, i-1]=b$), thus:

$$f(i, b)=1 \tag{2}$$

In the general case $b \in B_1$ and $|b|<M$ we must consider the bit in R preceding b:

$$f(i, b)=(1-p)f(i, 0b)+pf(i, 1b) \tag{3}$$

where "0b" is a bit string b, preceded by a 0-bit, and "1b" is a bit string b, preceded by a 1-bit.

Now we are ready to describe the dynamic programming algorithm for computing all f (i, b) for $M \le i \le L$ and $b \in B_1$.

Figure 7:
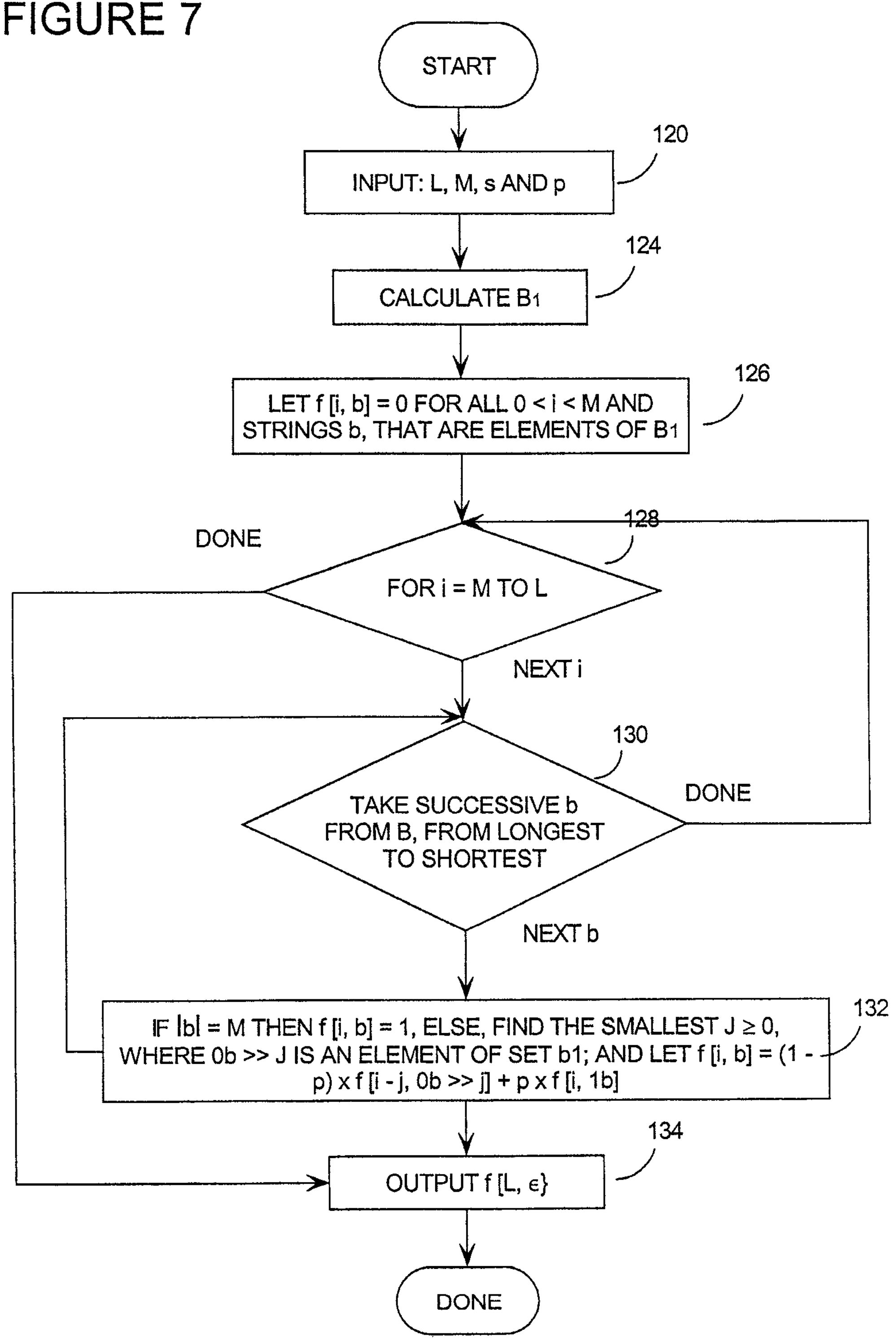
FIG. 7 presents a flow chart of a method of generating optimal seeds in an exemplary embodiment of the invention.

The process begins at step 120 of FIG. 7 where the user inputs a test seed s, the length of the seed model M, the length L of the homologous region and the homology level for this region, p.

Set $B_1$ is then computed at step 124. The following pseudo code can be used to compute $B_1$:

```
Initialize B1 to be an empty set;
For i from 1 to M do
Let s' be the length i suffix of the model s;
Let x and y be integers whose binary forms are s';
Repeat
   x=(x+1)|y;
   add the length i binary form of x to B1;
Until (x==2^i−1);
```

(In the pseudo code, the "|" is a sign means bitwise-or operation.)

The elements of array f[i, b] are then set to 0 at step 126, and conditions are then ready for calculating the probability that s hits the region.

We do this by looping through steps 128-134, until we detect at step 128 that we have considered all of the possible positions for which M can be placed in L. For each possible position (we call i), we consider each successive b from $B_1$, from longest to shortest, at step 130. At step 132, we then calculate the following:

```
if |b|=M then f[i, b]=1;
else
let j>0 be the least numbers such that 0b>>j∈B1;
let f[i, b]=(1−p)×f[i−j,0b>>j]+p×f[i, 1];
```

When step 132 has been completed for a given b, control returns to step 130, so that the remaining values of b can be considered. Once this calculation has been performed for every b, step 130 will return control to step 128. When all i have been considered, f[L, ϵ] can be output at step 134.

The correctness of the algorithm follows directly from Formulas (2), (3) and (1). Because $|B_1|<M2^{M-W}$, the algorithm requires $O(M_2 2^{M-W} L)$ time. When M−W=O (log L), the dynamic programming requires polynomial time.

The algorithm of FIG. 7 is repeated for all test seeds of interest until the optimal seed is determined. Next, hit generation can be performed per FIG. 8.

This embodiment of the invention uses a method for generating hits comparable to MegaBlast, thus it will not be described in great detail. Firstly step through each position in the target sequence by loop through steps 140-144, of FIG. 8. For each position, we compute a hash value from fitting the model at that particular position per step 142. We then insert that position into a hash table H at step 144, based on the hash value.

Once all positions of the target sequence have been considered, control passes from step 140 to step 146. Now, for each position in the query sequence (looping per step 146), we calculate a hash value x from fitting the optimized seed model at the current position, at step 148.

Then at step 150, we consider whether there are any positions j of the target sequence, such that the hash value (computed at step 142) is equal to x (computed at step 148). This can be done very efficiently by looking up the hash table H with the hash value x. When we have a match, we have a hit, which is reported at step 152. When all positions have been checked, control returns to step 146 so that other positions in the query sequence can be checked. Once it has been determined at step 146 that all positions have been checked, we exit this routine.

Figure 8:
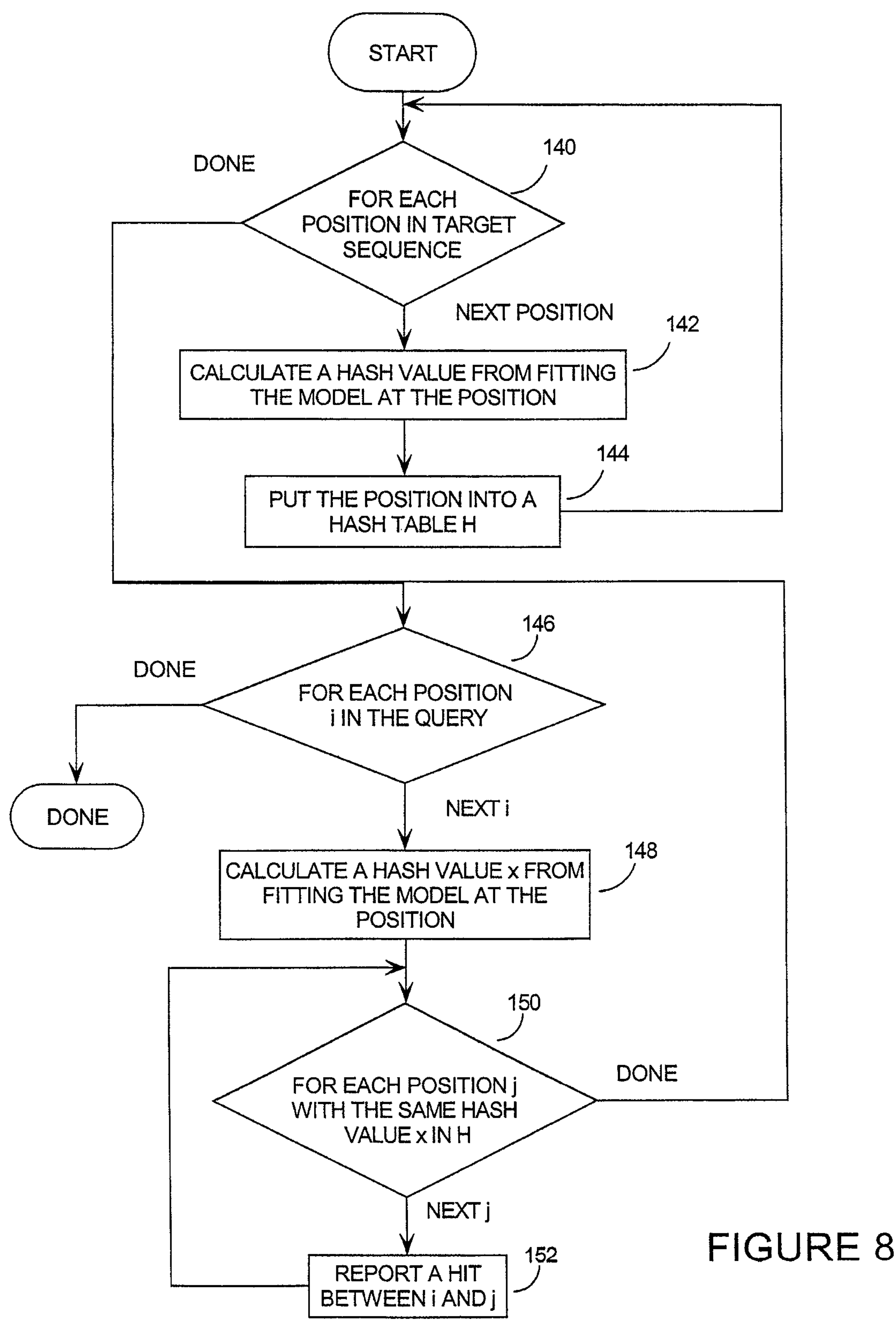
FIG. 8 presents a flow chart of a method of generating hits in an exemplary embodiment of the invention.
Figure 9:
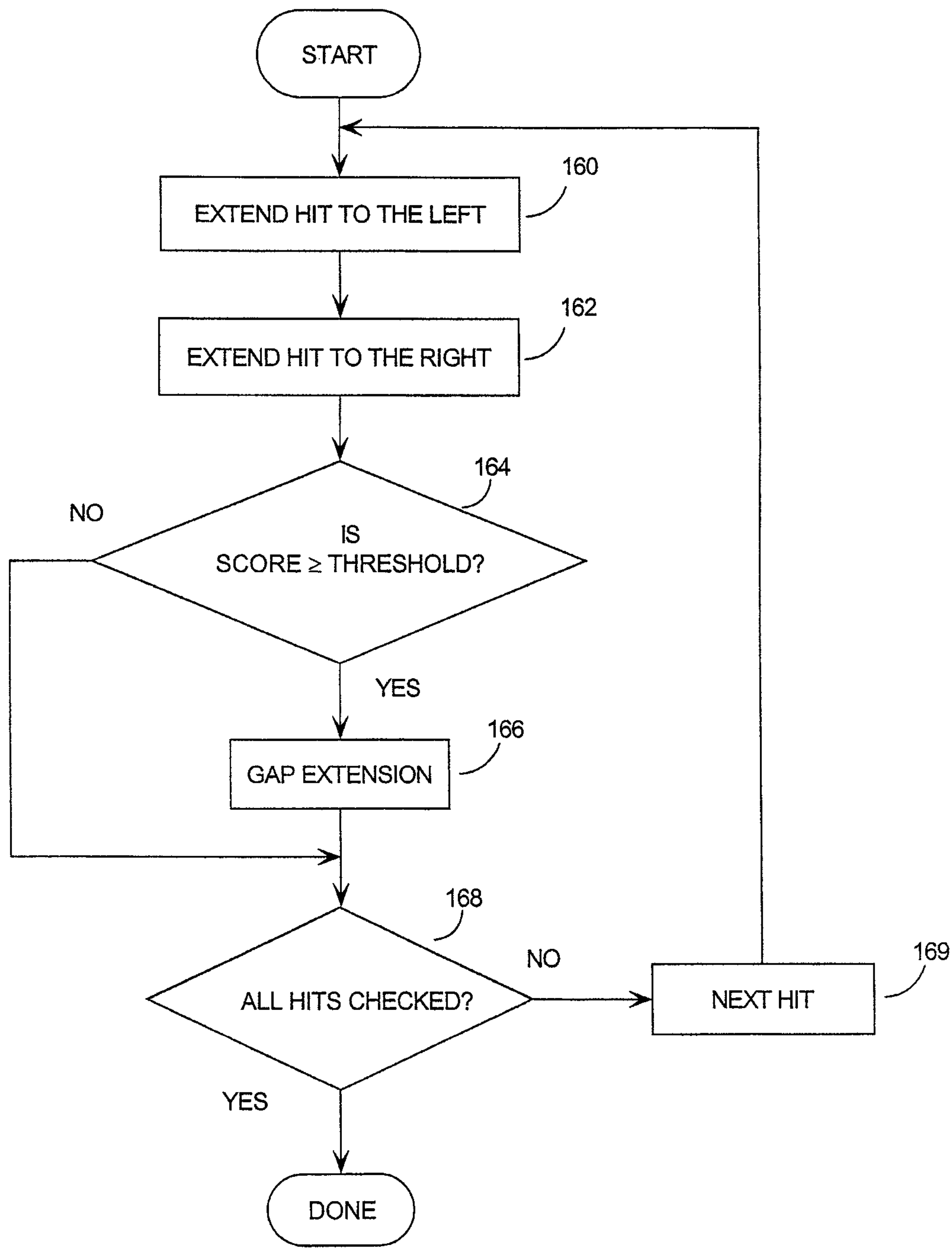
FIG. 9 presents a flow chart of a method of extending hits in an exemplary embodiment of the invention.

Once a hit has been determined per FIG. 8, it can be extended as shown in FIG. 9.

Each hit is extended in a greedy fashion in one direction, then the other per steps 160 and 162, stopping when the score drops by a certain amount. If the resulting segment pair is determined at step 164 to have a score below a certain minimum, then it is ignored (i.e. control passes to step 168 so that other hits can be considered), otherwise, it is determined to be a Highscoring Segment Pair (HSP). The following pseudo code can be used to do the extension to the right direction (step 162). The extension to the left direction can be done similarly:

```
Let i and j be the hit positions in query and target;
Let bestscore = 0; besti = i; bestj = j; score = 0;
Repeat
    i = i+1; j = j+1; score = score+scoreOf(query[i], target[j]);
    if(score>bestscore) then
        bestscore=score; besti=i; bestj=j;
        endif;
    until (score < bestscore − dropoff);
    besti and bestj are the boundaries of the extension;
```

Figure 10:
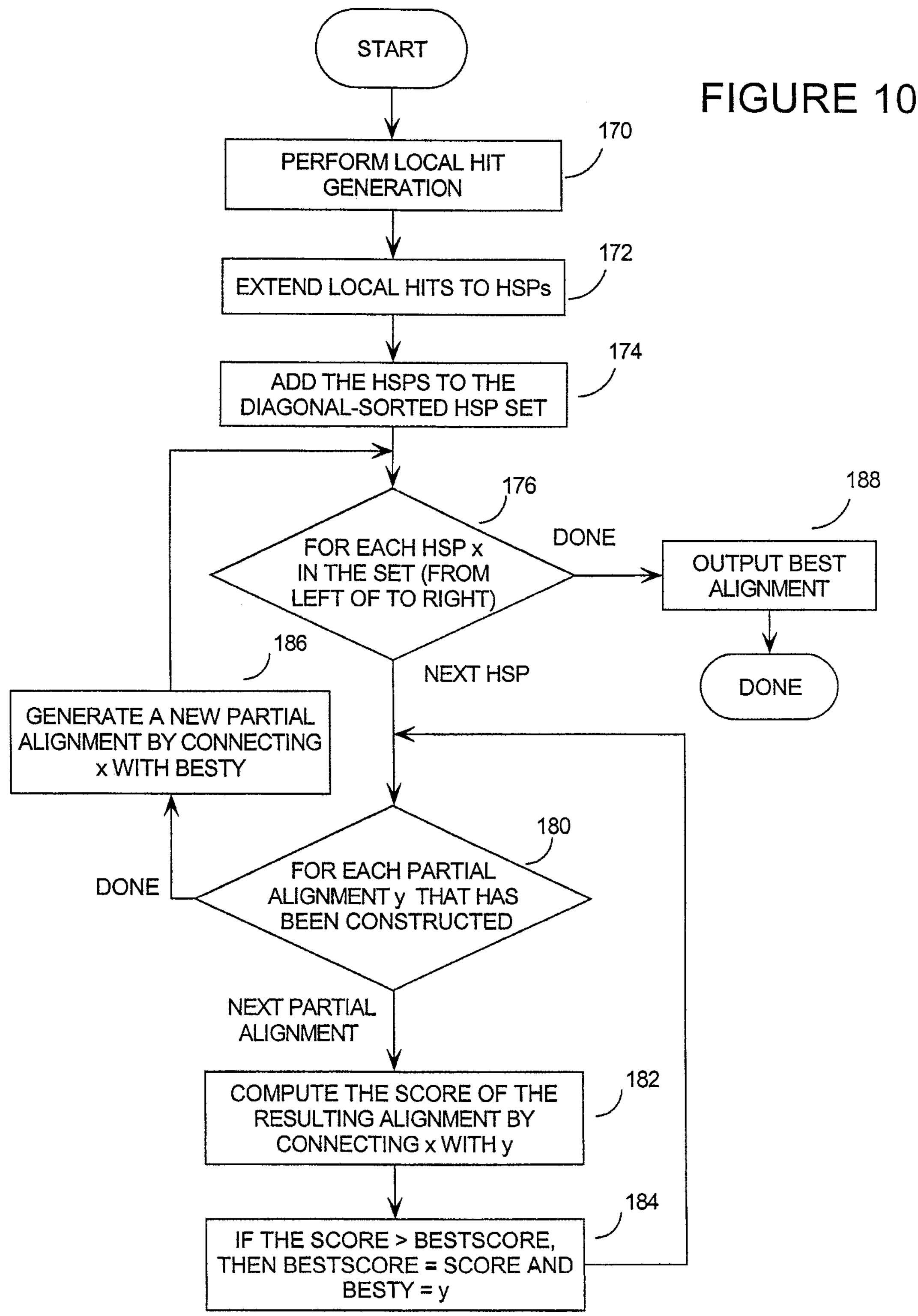
FIG. 10 presents a flow chart of a method of extending hits across gaps in an exemplary embodiment of the invention.

If it is determined at step 164 that the current hit is a HSP, then the gap is extended per step 166 (this process is described in detail with respect to FIG. 10). Control then passes to step 168. If it is determined at step 168 that all hits have been considered, the routine is complete, otherwise, the next hit is addressed per step 169, and control returns to step 160 so that the current hit can be analysed.

A method of gapping extensions using local hits will now be described with respect to the flow chart of FIG. 11.

When an HSP is being gap-extended to alignments, first local hits and local HSPs are generated at step 170. A local hit is a seed match generated using shorter seed models, and local HSPs are generated by extending the local hits. For clarity, the ordinary hits are called global hits here. By default, the exemplary embodiment of the invention uses 1101 as local seed model for the generation of local hits. A local hash table, which is similar to the hash table for the generation of global hits, is generated first, using the local seed model. The local hash table only indexes one of the two sequences at the neighborhood of the HSP. Then, local hits are generated by looking up the local hash table, in the same manner that the global hits are generated.

Local HSPs are also generated at step 172, in the same manner that the global HSPs are generated. By default, the exemplary embodiment of the invention will do the extension to generate an HSP once there are three local hits in the same diagonal and close to each other. Once a new HSP is generated, it is added into the set of diagonal-sorted HSPs at step 174. A red-black tree is used to implement the set of HSPs sorted by diagonal (red-black trees are well known in the art of computer science).

To build the gapped alignment, we do a gap-left extension for each HSP in the region. We start from the left-most HSP to the right-most HSP in the region; control step 176 allows us to loop through steps 180-186 for successive HSPs (we call each success HSP x) until we have checked all HSPs. Once all HSPs have been checked, we will have found the best alignment, which can be output at step 188.

For each HSP, we consider all the HSPs to its left, by looking up the diagonal sorted set of HSPs. Because we do gap-left from left to right, each of them has already been gap-lefted and become a part of a partial alignment. We try to connect the current HSP to each partial alignment and compute the score of the resulted partial alignment. Then we choose the connection whose resulted partial alignment has the highest score as the gap-left extension of the current HSP.

After all the HSPs in the region have been gap-lefted, we obtain many alignments, among which, the one with the highest score is the one we want to output.

In other words, we incrementally check each partial alignment y per step 180, connecting it with the current HSP segment x (from step 176), and computing the score of this resulting alignment at step 182. At step 184, we keep a record of the highest score (bestscore) for this particular HSP x, and the partial alignment y that yields this highest score (besty).

Once it is determined at step 180 that all partial alignments y have been considered, control passes to step 186 where the new partial alignment is defined as the current x connected to the besty. The rest of the HSP x are then considered per step 176.

By default, the exemplary embodiment of the invention allows a maximum gap length of 256, which can be done quite efficiently with its diagonal ordered tree of recent HSPs, and often can be seen to make it use a single alignment where other programs output two separate ones.

The order of the steps in the gap extension described above can be different to the order presented in FIG. 10. For example, the gap-left can be done once a new local HSP is generated, instead of after all local HSPs being generated.

Adaptation to Amino Acids Sequence Homology Search

The same idea has been adopted and implemented for protein sequence homology search. When searching for homologies in a protein database, we compute the index table of the database similarly to the index table of DNA databases. The only difference is that the index for a particular position is an integer between 0 and $20^{weight}-1$.

The best weight for searching a protein database is on the order of $\log_{20} N$, where N is the number of amino acids in the protein database. For example, when searching in a database with at least 100M amino acids, the best weight of the model should be 6, not 3, which is used in BLAST. To achieve the same or better sensitivity level than BLAST with higher weight models, we can reduce the similarity level of hits. For example, using amino acid substitution matrix BLOSUM62, BLAST considers each pair of 3-mers with similarity score no less than 11 as a hit. With weight 6, we can consider each pair of 6-mers with similarity score no less than 15, rather than 11*2=22, as a hit.

Achievements of the Invention

Several test runs of the exemplary embodiment of the invention in comparison to other programs are reported here in order to demonstrate the power of the invention. Since the Blast family, especially the newly improved Blastn, is the industry standard, and widely recognized for its sensitivity (Blastn) and speed (MegaBlast), most of the comparisons will be limited to these programs. All experiments are performed on a 700 MHz Pentium III PC with 1 Gbyte of memory.

Table 1 below compares the method of the invention with the latest versions of Blastn and megaBlast, downloaded from the NCBI website. All programs were run without filtering (bl2seq option-F F) to ensure identical input to the actual matching engines.

TABLE 1

| Performance Comparisons | | | | |
|---|---|---|---|---|
| Comparing | PH | PH2 | MB28 | Blastn |
| *M. pneumoniae* (828 K) to *M. genitalium* (589 K) | 10 s/65 M | 4 s/48 M | 1 s/88 M | 47 s/45 M |
| *E. coli* (4.7 M) to *H. influenza* (1.8 M) | 34 s/78 M | 14 s/68 M | 5 s/561 M | 716 s/158 M |
| *A. thaliana* chr 2 (19.6 M) to *A. thaliana* chr 4 (17.5 M) | 5020 s/279 M | 498 s/231 M | 21720 s/1087 M | — |
| *H. sapiens* chr 22 (35 M) to *H. sapiens* chr 21 (26.2 M) | 14512 s/419 M | 5250 s/417 M | — | — |

If not specified, all of the above use a scoring of: match 1, mismatch −1, gap open −5, gap extension −1. "PH" denotes an embodiment of the called PatternHunter with seed weight 11, PH2 denotes same with double hit mode (sensitivity similar to Blast's single hit size 11 seed as shown in FIG. 5). MB28 denotes MegaBlast with default seed size 28, and default affine gap penalties. Blastn (via BL2SEQ) uses default seed size 11. Table entries under PH, PH2, MB28 and Blastn indicate time (seconds) and space (megabytes) used; the blank entries indicate that an out of memory or segmentation fault occurred.

Table 2 compares the method of the invention with SENSEI; note that SENSEI, as currently available, does not do any gapped alignments.

TABLE 2

| Performance Comparisons With SENSEI | | | |
|---|---|---|---|
| Comparing | PH (9) | PH (11) | SENSEI |
| *E. coli* (4.7 M) to *H. influenza* (1.8 M) | 279 s/ 67 M | 34 s/ 78 M | 780 s/ 64 M |
| *A. thaliana* chr 2 (19.6 M) to *A. thaliana* chr 4 (17.5 M) | 677 m/ 282 M | 84 m/ 279 M | 781 m/ 415 M |

This table compares exemplary runs of the PatternHunter algorithm with seed weights of 9 and 11 for a 1-hit model, compared to SENSEI's weight 8 seed. PatternHunter's weight 9 spaced seed has higher single-hit sensitivity than SENSEI's 8 as shown in FIG. 4.

Figure 11:
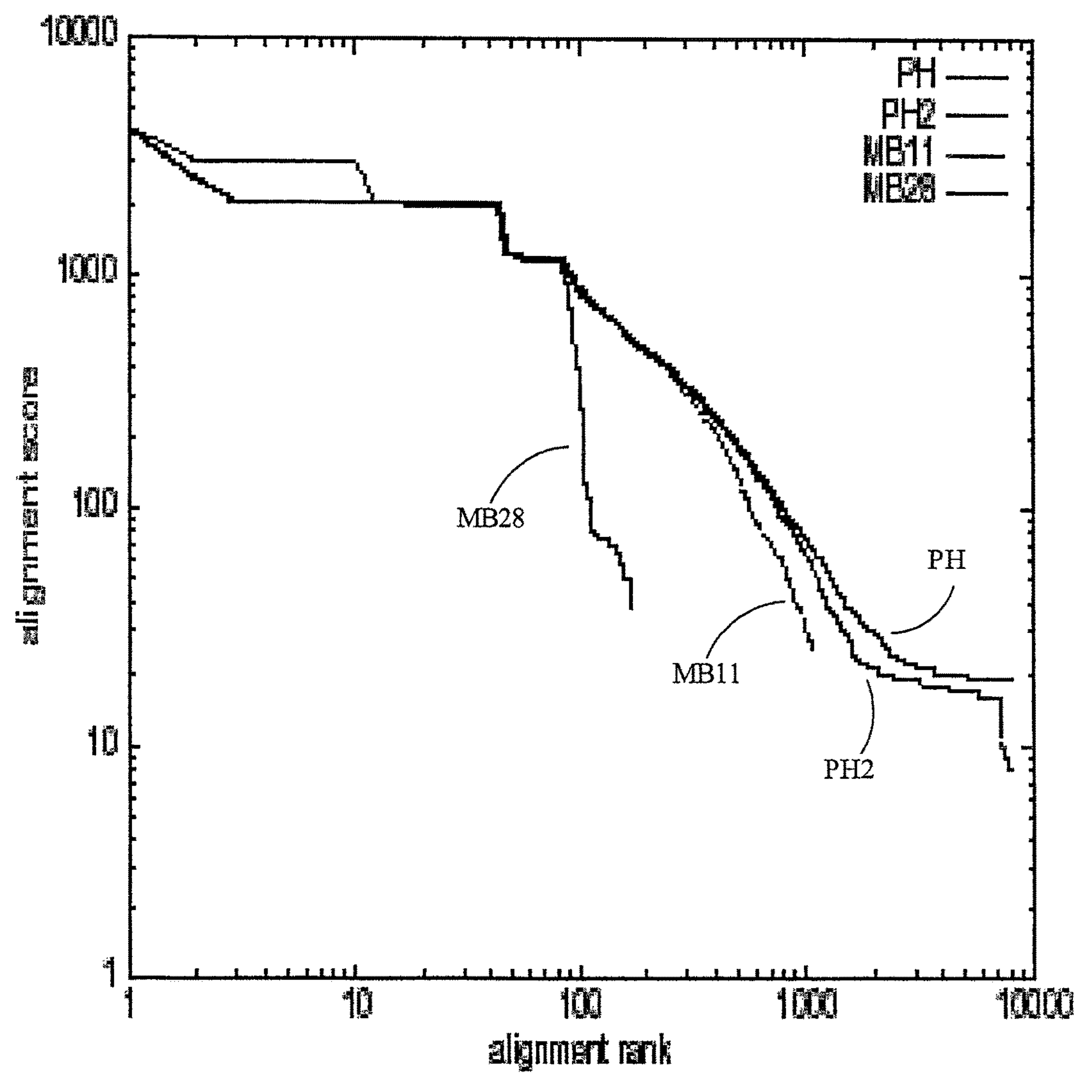
FIG. 11 presents a graph comparing the performance of an embodiment of the invention to MegaBlast, for *H. Influenza* vs. *E. Coli;*
Figure 12:
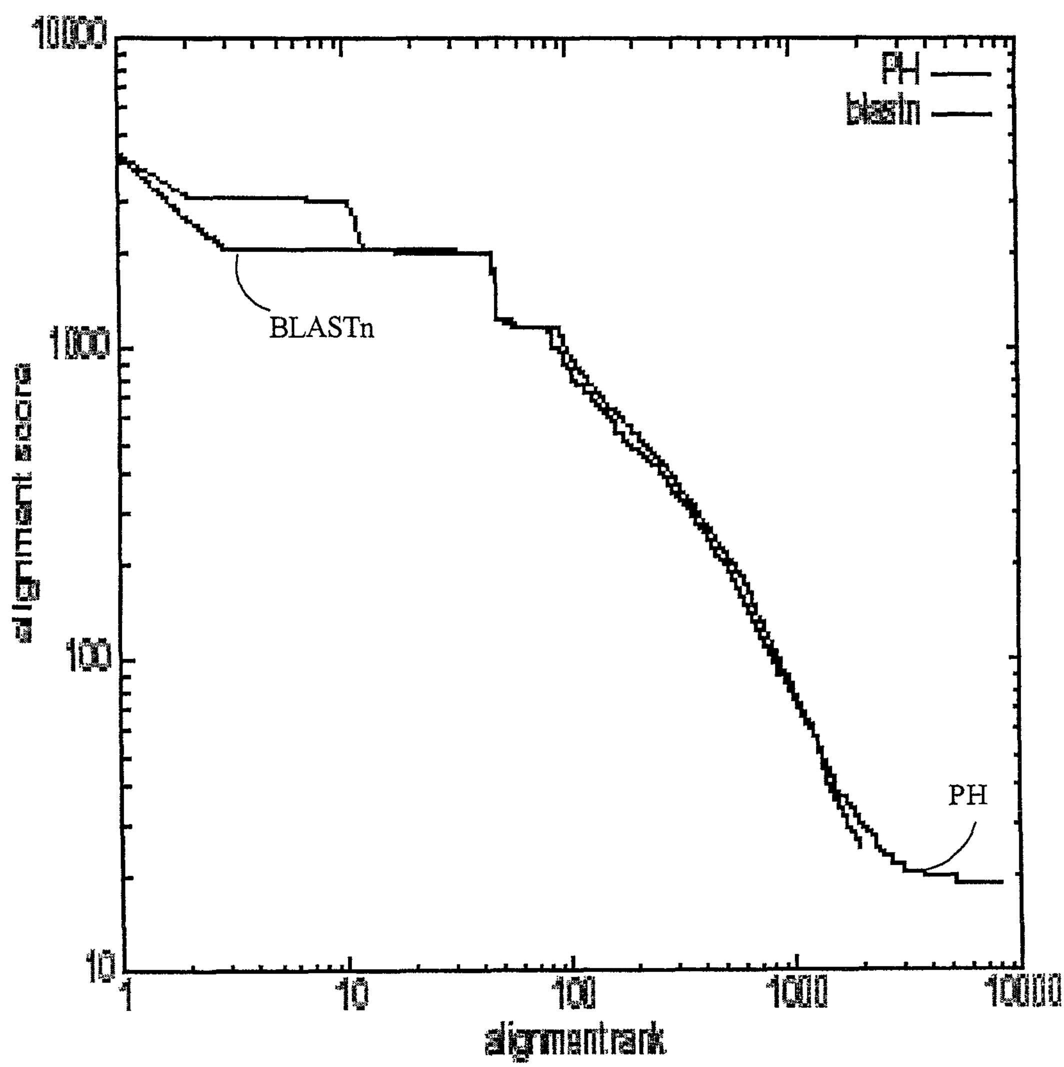
FIG. 12 presents a graph comparing the performance of an embodiment of the invention to blastn, for *H. Influenza* vs. *E. Coli*.
Figure 13:
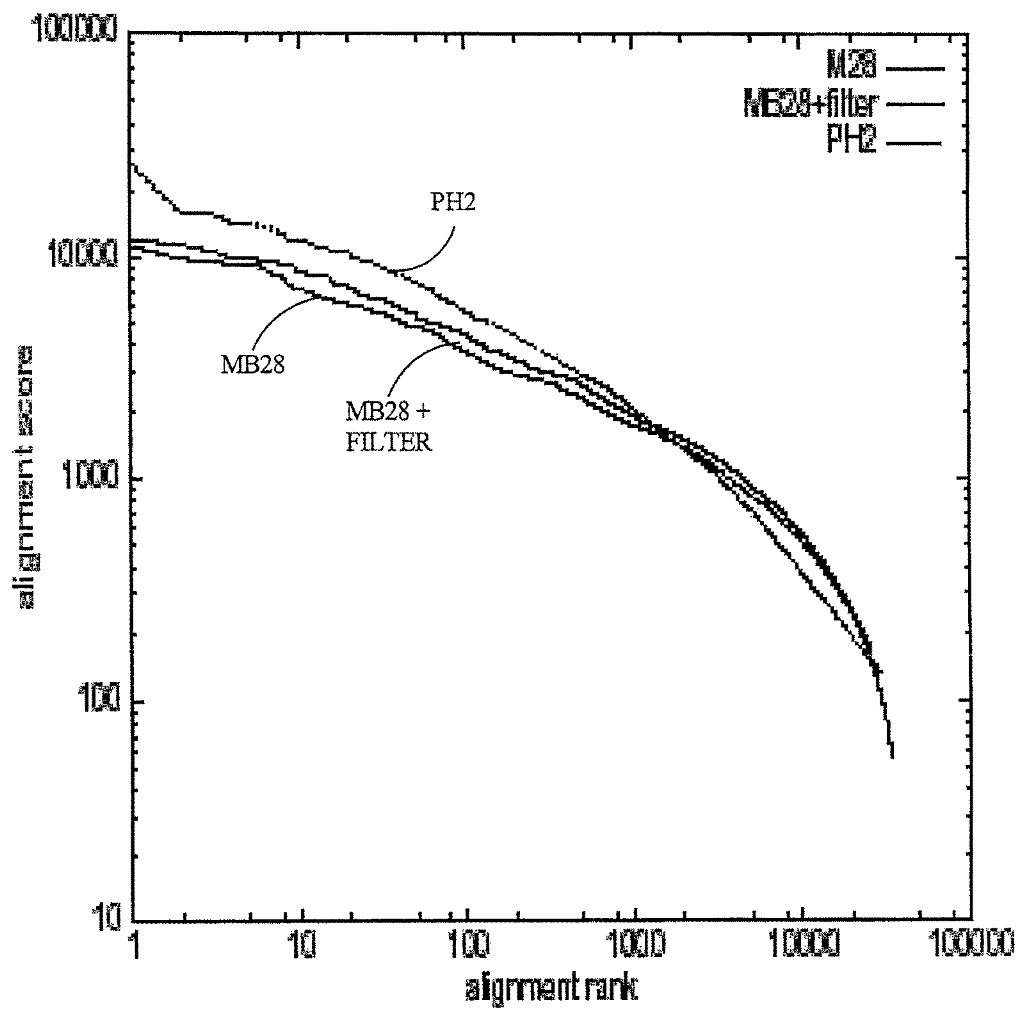
FIG. 13 presents a graph comparing the performance of an embodiment of the invention to MegaBlast, for *A. thaliana* chr2 vs. chr4.

One may suspect that the method of the invention sacrifices quality for speed, however, FIGS. 11, 12 and 13 show the opposite.

*H. Influenza* and *E. Coli* were used as the input sequences for the tests in FIG. 11. Score is plotted as a function of the rank of the alignment, with both axes logarithmic. Clearly, FIG. 11 shows that MegaBlast using seed weight 28 (MB28) misses over 700 high scoring alignments of score at least 100. MB11 is MegaBlast with seed size 11 (50 times slower and 10 times more memory use than PH2), indicating that the missed alignments by MB28 are mainly due to seed size.

Using the same parameters (i.e. *H. Influenza* and *E. Coli* as the input sequences, etc.), PatternHunter outputs better results than Blastn as shown in FIG. 12, is 20 times faster and uses one tenth the memory. Notice the quick growth of Blastn/MegaBlast time/space requirements, indicating poor scalability.

Only MegaBlast (MB28) at its default affine gap costs allowed further comparison without running out of memory, but with vastly inferior output quality compared to PatternHunter (PH2), which uses only one fifth the time and one quarter the space, as shown in FIG. 13. While MegaBlast is designed for high speed on highly similar sequences and Blastn for sensitivity, PatternHunter simultaneously exceeds Blastn in sensitivity, MegaBlast in speed (on long sequences), and both in memory use.

In the *A. thaliana* chr2 and chr4 test of FIG. 13, PatternHunter (PH2) outscores MegaBlast in one sixth of the time and one quarter the memory. Both programs used MegaBlast's non-affine gap costs (with gapopen 0, gapextend −7, match 2, and mismatch −6) to avoid MegaBlast from running out of memory. For comparison we also show the curve for MegaBlast with its default low complexity filtering on, which decreases its runtime more than sixfold to 3305 seconds.

Additional Options and Alternatives

Clearly, the invention could be applied to other biological homology search tools and techniques. For example, the invention could be applied to any manner of biological sequences including: DNA sequences such as genomes, chromosomes, RNA sequences, ESTs, cDNAs, short and long fragments, or Protein (amino acid) sequences.

While particular embodiments of the present invention have been shown and described, it is clear that changes and modifications may be made to such embodiments without departing from the true scope and spirit of the invention. It is also clear that the present invention also applies to homology searching in protein (amino acid) sequences.

The method steps of the invention may be embodied in sets of executable machine codes stored in a variety of formats such as object code or source code. Such code is described generically herein as programming code, or a computer program for simplicity. Clearly, the executable machine code may be integrated with the code of other programs, implemented as subroutines, by external program calls, implemented in the hardware circuit, or by other techniques as known in the art.

The embodiment of the invention may be executed by a computer processor or similar device programmed in the manner of method steps, or may be executed by an electronic system which is provided with means for executing these steps. Similarly, an electronic memory medium such as computer diskettes, CD-Roms, Random Access Memory (RAM), Read Only Memory (ROM) or similar computer software storage media known in the art, may store software code executable to perform such method steps. As well, electronic signals representing these method steps may also be transmitted via a communication network.

The invention could for example be applied to personal computers, super computers, main frames, application service providers (ASPs), Internet servers, smart terminals or personal digital assistants. Again, such implementations would be clear to one skilled in the art, and do not take away from the invention.

What is claimed is:

1. A computer-implemented method for performing homology searching through comparing a first string of electronically represented target biological sequence data and a second string of electronically represented query biological sequence data to identify one or more sections of alignments between the first string and the second string, the method comprising:

accessing a library comprised of one or more data structures, each of the one or more data structures configured to store one or more binary mask strings indicative of sequence data positions where a match is required at that sequence data position and sequence data positions where a match is not required at that sequence data position, each of the one or more binary mask strings having a weight determined by a number of sequence data positions where a match is required, and a length determined by a total number of sequence data positions in the binary mask string;

generating one or more proposed binary mask models by populating each of the one or more data structures with a corresponding proposed binary mask string, each proposed binary mask string representing a possible non-consecutive spaced mask model having a predefined weight and a predefined length;

determining which data structure of the one or more data structures is populated with an optimal binary mask string having a highest likelihood of identifying hits in a random pair of similar regions between the first string and the second string of biological sequence data being searched the optimal mask string being computationally identified by processing the one or more data structures to identify a data structure that maximizes the probability that a seed match is found, the probability characterized by the recursive relation:

$$\text{Probability } (s \text{ matches } R)=\text{Sum}\{\text{for all } |b|=M\} \text{ Probability } (b)\, f(L-M, b),$$

where f(i,b)=1, if s=b, otherwise f(i,b)=(1−p)f(i−1, 0b')+pf(i−1,1b') where b' is b having a last bit deleted, and where s is a mask, M is a length of the mask s, and f(i,b) is the probability that mask s matches the length i prefix of R, where R is a random string of length L, that ends with b, where b is a binary string, and where p is a probability of a bit in the binary string b to be a character indicating that a match is required;

converting the first string into a reduced target sequence array by:

for each position of the first string:

identifying a substring of the first string starting at the position being iterated;

generating a masked string by masking the substring of the first string with the optimal binary mask string;

hashing the masked string to generate a reduced target sequence value; and storing the reduced target sequence value at an array index corresponding to the position of the first string associated with the reduced target sequence value;

determining one or more pairs of locations indicative of probable alignments between the first string and the second string by;

for each position of he second string:

identifying a substring of the second string starting at the position being iterated;

generating a masked string by masking the substring of the second string with the optimal binary mask string;

hashing the masked string to generate a reduced query sequence value; and determining whether the reduced query sequence value exits in the reduced target a sequence array;

upon determining that the reduced query sequence value exists in the reduced target sequence array, flagging a pair of locations between the first string and the second string as indicative of a probable alignment between the first string and the second string; and processing each pair locations of the one or more flagged pairs of locations to determine the one or more sections of alignments between the first string and the second string.

2. The method of claim 1, further comprising extending the one or more sections of alignments between the first string and the second string to identify longer alignments between the first string and the second string.

3. The method of claim 1, wherein each binary mask string of the one or more binary mask strings includes one or more characters indicative of positions; wherein a match is required at that position are "1" characters, and wherein the characters indicative of positions where no match is required at that position are "0" characters.

4. The method of claim 3, wherein the optimal binary mask string is 111010010100110111 or its mirror image 111011001010010111.

5. The method of claim 1, wherein each binary mask string of the one or more binary mask strings comprises non-consecutive matches.

6. The method of claim 1, wherein the optimal binary mask string has a length of 18, and includes characters requiring matches only at the first three positions, the fifth position, the eight position, the tenth position, the thirteenth and fourteenth positions, and the sixteenth to the eighteenth position.

7. An electronic computer system for performing homology searching through comparing a first string of electronically represented target biological sequence data and a second string of electronically represented query biological sequence data to identify one or more sections of alignments between the first string and the second string, the system comprising:

an input device configured to receive the first string and the second string of biological sequence data;

a non-transitory computer readable memory storing a library comprised of one or e data structures, each of the one or more data structures configured to store one or more binary mask strings indicative of sequence data positions where a match is required at that sequence data position and sequence data positions where a match is not required at that sequence data position, each of the one or more binary mask strings having a weight determined by a number of sequence data positions where a match is required, and a length determined by a total number of sequence data positions in the binary mask string;

a homology search processor configured to:

generate one or more proposed binary mask models by populating each of the one or more data structures with a corresponding proposed binary mask string, each proposed binary mask string representing a possible non-consecutive spaced mask model having a predefined weight and a predefined length;

determine which data structure of he one or more data structures is populated with an optimal binary mask string having a highest likelihood of identifying hits in a random pair of similar regions between the first string and the second string of biological sequence data being searched, the optimal binary mask string being computationally identified by processing the one or more data structures to identify a data structure that maximizes the probability that a match is found, the probability characterized by the recursive relation:

$$\text{Probability } (s \text{ matches } R)=\text{Sum}\{\text{for all } |b|=M\} \text{ Probability } (b)\, f(L-M,\, b),$$

where f(i,b)=1, if s=b, otherwise f(i,b)=(1−p)f(i−1, 0b')+pf(i−1,1b') where b' is b having a last bit deleted, and where s is a mask, M is a length of the mask s, and f(i,b) is the probability that mask s matches the length i prefix of R, where R is a random string of length L, that ends with b, where b is a binary string, and where p is a probability of a bit in the binary string b to be a character indicating that a match is required;

convert the first string into a reduced target sequence array by;

for each position of the first string:

identifying a substring of the first string starting at the position being iterated;

generating a masked string by masking the substring of the first string with the optimal binary mask string;

hashing the masked string to generate a reduced target sequence value; and storing the reduced target sequence value at an array index corresponding to the position of the first string associated with the reduced target sequence value;

determine one or more pairs of locations indicative of probable alignments between the first string and the second string by:

for each position of the second string:

identifying a substring of the second string starting at the position being iterated;

generating a masked string by masking the substring of the second string the optimal binary mask string;

hashing the masked string to generate a reduced query sequence value; and determining whether the reduced query sequence value exist in the reduced target sequence array;

upon determining that the reduced query sequence value exists in the reduced target sequence array, flagging a pair of locations between the first string and the second string as indicative of a probable alignment between the first string and the second string; and process each pair of locations of the one or more flagged pairs of locations to determine the one or more sections of alignments between the first string and the second string.

8. A computer-implemented method of performing a homology search on one or more processors, the homology search being configured such that a non-consecutive search seed is utilized in processing a first string of target biological sequence data and a second string of query biological sequence data to determine one or more sections of alignments between the first string and the second string, the method comprising:

accessing a library comprised of one or more data structures, each of the one or more data structures configured to store one or more binary mask strings indicative of sequence data positions where a match is required at that sequence data position and sequence data positions where a match is not required at that sequence data position, each of the one or more binary mask strings having a weight determined by a number of sequence data positions where a match is required, and a length determined by a total number of sequence data positions in the binary mask string;

receiving an optimal mask string computationally identified by processing the one or more data structures to identify a data structure that maximizes the probability that a seed match is found using a recursive relation;

converting the first string into a reduced target sequence array by:

for each position of the first string:

identifying a substring of the first string starting at the position being iterated;

generating a masked sting by masking the substring of the first string with the optimal binary ask string;

hashing the masked string to generate a reduced target sequence value; and storing the reduced target sequence value at an array index corresponding to the position of the first string associated with the reduced target sequence value;

determining one or more pairs of locations indicative of probable alignments between the first string and the second string by:

for each position of the second string:

identifying a substring of the second string starting at he position being iterated, generating a masked string by masking the substring of the second string with the optimal binary mask string;

hashing the masked string to generate a reduced query sequence value; and determining whether the reduced query sequence value exists in the reduced target sequence array;

upon determining that the reduced query sequence value exists in the reduced target sequence array, flagging a pair of locations between the first sting and the second string as indicative of a probable alignment between the first string and the second string; and process each pair of locations of the one or more flagged pairs of locations to determine the one or more sections of alignments between the first string and the second string;

wherein the optimal mask string is a string of characters, indicative of positions where a match is required at that position, and positions where a match is not required at that position; and wherein the non-consecutive search seed has a length of 18 positions for matching, and includes characters requiring matches only at the first three positions, the fifth position, the eight position, the tenth position, the thirteenth and fourteenth positions, and the sixteenth to the eighteenth position or a mirror image thereof.

9. The method of claim 8, wherein the characters indicative of positions where a match is required at that position are "1" characters, and wherein the characters indicative of positions where no match is required at that position are "0" characters; and wherein the optimal mask string is 111010010100110111 or its mirror image 111011001010010111.

* * * * *

```
                         SEQUENCE LISTING


<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Example Sequence
<300> PUBLICATION INFORMATION:
<301> AUTHORS: Li, Ming
      Ma, Bin
      Tromp, John
<302> TITLE: Method and system for faster and more sensitive homology
      searching

<400> SEQUENCE: 1

aatgagatag accttta                                                  17


<210> SEQ ID NO 2
<211> LENGTH: 15
<212> TYPE: DNA
<213> ORGANISM: Artificial Sequence
<220> FEATURE:
<223> OTHER INFORMATION: Example Sequence
<300> PUBLICATION INFORMATION:
<301> AUTHORS: Li, Ming
      Ma, Bin
      Tromp, John
<302> TITLE: Method and system for faster and more sensitive homology
      searching

<400> SEQUENCE: 2

aattatagtc cttta                                                    15
```